(12) United States Patent
Anderson et al.

(10) Patent No.: US 9,044,279 B2
(45) Date of Patent: Jun. 2, 2015

(54) DEVICE AND METHOD FOR EXPANDING THE SPINAL CANAL WITH SPINAL COLUMN STABILIZATION AND SPINAL DEFORMITY CORRECTION

(75) Inventors: D. Greg Anderson, Moorestown, NJ (US); Barry Turner, Columbus, IN (US); David Spenciner, North Attleboro, MA (US)

(73) Assignee: Innovative Surgical Designs, Inc., Bloomington, IN (US)

(*) Notice: Subject to any disclaimer, the term of this patent is extended or adjusted under 35 U.S.C. 154(b) by 615 days.

(21) Appl. No.: 13/074,169

(22) Filed: Mar. 29, 2011

(65) Prior Publication Data

US 2011/0230915 A1    Sep. 22, 2011

Related U.S. Application Data

(63) Continuation-in-part of application No. 12/624,946, filed on Nov. 24, 2009, now abandoned, which is a continuation-in-part of application No. 11/656,790, filed on Jan. 22, 2007, now abandoned, which is a (Continued)

(51) Int. Cl.
| | |
|---|---|
| *A61B 17/56* | (2006.01) |
| *A61B 17/70* | (2006.01) |
| *A61B 17/86* | (2006.01) |

(52) U.S. Cl.
CPC .......... *A61B 17/7071* (2013.01); *A61B 17/7001* (2013.01); *A61B 17/8665* (2013.01); *A61B 17/8685* (2013.01)

(58) Field of Classification Search
CPC ........... A61B 17/7071; A61B 17/7001; A61B 17/8665; A61B 17/8685

USPC ............ 606/63, 68, 246, 248, 250, 251, 258, 606/259, 301, 305, 308, 90, 105; 623/17.11, 17.15, 17.16
See application file for complete search history.

(56) References Cited

U.S. PATENT DOCUMENTS

| | | | |
|---|---|---|---|
| 2,244,683 | A | 6/1941 | Fisher |
| 2,261,230 | A | 11/1941 | Cox et al. |

(Continued)

FOREIGN PATENT DOCUMENTS

| | | |
|---|---|---|
| AU | 516581 | 6/1981 |
| JP | 11004840 | 1/1999 |

(Continued)

OTHER PUBLICATIONS

Patent Abstracts of Japan, vol. 2000; No. 09, Oct. 13, 2000, and JP2000152951, Jun. 6, 2000 (abstract).

(Continued)

*Primary Examiner* — Pedro Philogene
*Assistant Examiner* — David Comstock
(74) *Attorney, Agent, or Firm* — Blank Rome LLP

(57) ABSTRACT

Spinal canal expansion through pedicle lengthening in combination with spinal column stabilization, to treat spinal stenosis, spondylolisthesis, kyphosis, scoliosis or a major spinal rotational deformity, with or without a spinal fusion. A device or implant that includes a pedicle lengthening implant to decompress (expand) the spinal canal, and a bridge to connect two or more pedicle lengthening implants and/or pedicle screws or bone anchors to achieve simultaneous spinal stabilization across one or more vertebral segments. The bridge across the vertebral segments can include a longitudinal member, such as a plate or rod. The pedicle lengthening implant is originally made, or can be modified to, connect to the longitudinal member. Spinal deformity can be manipulated, through operation of one or more pedicle lengthening implants in respective vertebral segments, to improve a relative relationship between the respective vertebra segments, the longitudinal member then fixating the vertebral segments into a multi-level spinal construct.

23 Claims, 8 Drawing Sheets

Related U.S. Application Data continuation of application No. 10/102,525, filed on Mar. 19, 2002, now Pat. No. 7,166,107.

(60) Provisional application No. 61/117,726, filed on Nov. 25, 2008, provisional application No. 61/318,441, filed on Mar. 29, 2010.

(56) References Cited

U.S. PATENT DOCUMENTS

| | | |
|---|---|---|
| 3,174,387 A | 3/1965 | Fischer |
| 3,896,504 A | 7/1975 | Fischer |
| 4,013,071 A | 3/1977 | Rosenberg |
| 4,716,893 A | 1/1988 | Fischer et al. |
| 4,917,704 A | 4/1990 | Frey et al. |
| 4,955,908 A | 9/1990 | Frey et al. |
| 5,034,011 A | 7/1991 | Howland |
| 5,059,193 A | 10/1991 | Kuslich |
| 5,108,404 A | 4/1992 | Scholten et al. |
| 5,176,678 A | 1/1993 | Tsou |
| 5,258,031 A | 11/1993 | Salib et al. |
| 5,263,803 A | 11/1993 | Anquetin |
| 5,425,772 A | 6/1995 | Brantigan |
| 5,480,440 A | 1/1996 | Kambin |
| 5,489,210 A | 2/1996 | Hanosh |
| 5,496,322 A | 3/1996 | Mathews |
| 5,653,762 A | 8/1997 | Pisharodi |
| 5,653,763 A | 8/1997 | Errico et al. |
| 5,722,977 A | 3/1998 | Wilhemy |
| 5,725,527 A | 3/1998 | Biedermann et al. |
| 5,766,251 A | 6/1998 | Koshino |
| 5,772,663 A | 6/1998 | Whiteside et al. |
| 5,827,285 A | 10/1998 | Bramlet |
| 5,836,948 A | 11/1998 | Zucherman et al. |
| 5,964,761 A * | 10/1999 | Kambin ............ 606/304 |
| 5,980,572 A | 11/1999 | Kim et al. |
| 6,008,433 A | 12/1999 | Stone |
| 6,009,531 A | 12/1999 | Selvidge et al. |
| 6,018,094 A | 1/2000 | Fox |
| 6,077,268 A | 6/2000 | Farris et al. |
| 6,080,157 A | 6/2000 | Cathro et al. |
| 6,099,531 A | 8/2000 | Bonutti |
| 6,129,763 A | 10/2000 | Chauvin et al. |
| 6,224,599 B1 | 5/2001 | Baynham et al. |
| 6,248,106 B1 | 6/2001 | Ferree |
| 6,270,501 B1 | 8/2001 | Freiberg et al. |
| 6,358,254 B1 | 3/2002 | Anderson |
| 6,402,750 B1 | 6/2002 | Atkinson |
| 6,428,256 B2 | 8/2002 | Wieser |
| 6,610,091 B1 | 8/2003 | Reiley |
| 6,635,087 B2 | 10/2003 | Angelucci et al. |
| 7,166,107 B2 | 1/2007 | Anderson |
| 2003/0028251 A1 | 2/2003 | Mathews |
| 2003/0212400 A1 | 11/2003 | Bloemer et al. |
| 2006/0241774 A1 | 10/2006 | Attali et al. |
| 2007/0219555 A1 | 9/2007 | Anderson |
| 2008/0221623 A1 | 9/2008 | Gooch |
| 2010/0168751 A1 | 7/2010 | Anderson |
| 2010/0198277 A1 | 8/2010 | Anderson |

FOREIGN PATENT DOCUMENTS

| | | |
|---|---|---|
| JP | 2000139970 | 5/2000 |
| JP | 2000152951 | 6/2000 |
| JP | 2001079024 | 3/2001 |
| WO | WO97/09940 | 3/1997 |

OTHER PUBLICATIONS

Patent Abstracts of Japan, vol. 2000, No. 08, Oct. 6, 2000, and Jp 2000139970, May 23, 2000 (abstract).

Patent Abstracts of Japan, vol. 1999, No. 04, Apr. 30, 1999, and JP11004840, Jan. 12, 1999 (abstract).

International Search Report and Written Opinion; International Application No. PCT/US2009/065869; International Filing Date Nov. 25, 2009; 10 pages.

International Search Report; International Application No. PCT/US03/08565; International Filing Date Mar. 19, 2003; 3 pages.

First Examination in Australia Patent Application No. 2003220421 (now patented); Oct. 17, 2007 and Reply dated Nov. 12, 2008; 4 pages.

International Preliminary Report on Patentability. International Application No. PCT/US2003/008565; dated Mar. 2, 2010; 3 pages.

International Preliminary Report on Patentability; International Application No. PCT/US2009/065869; dated May 31, 2011; 9 pages.

* cited by examiner

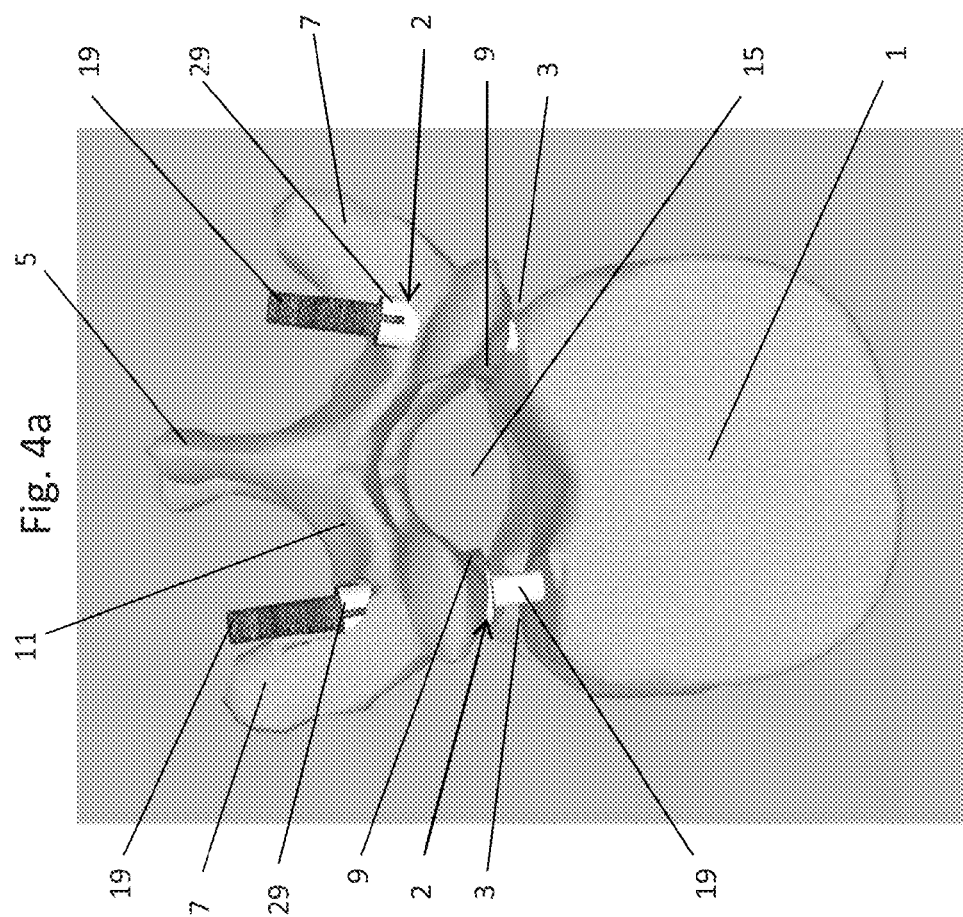

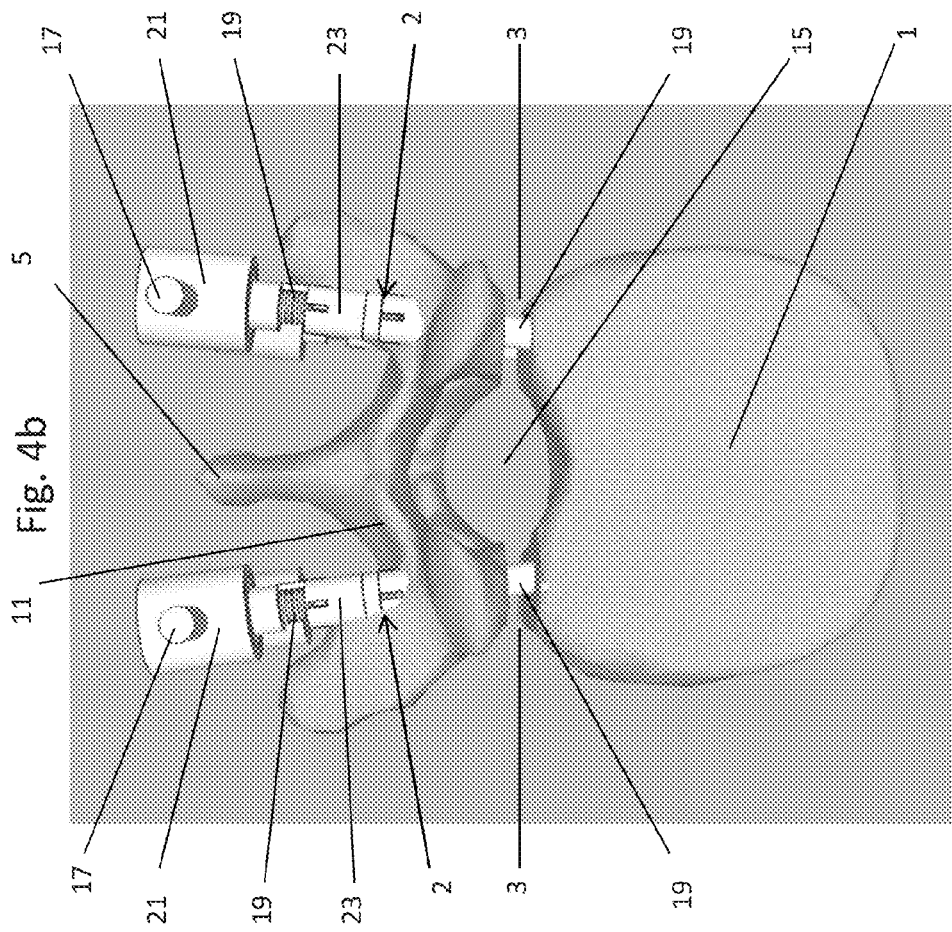

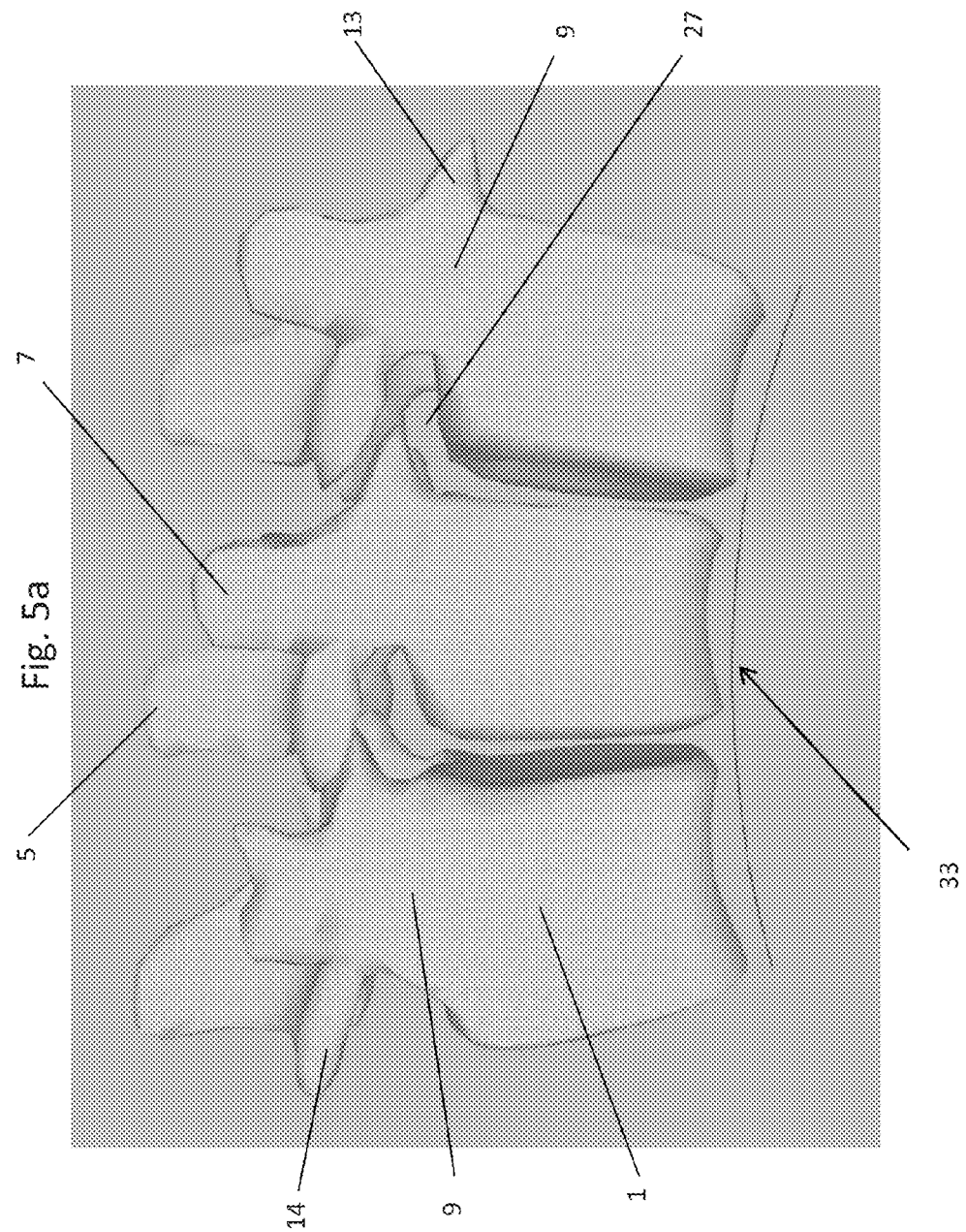

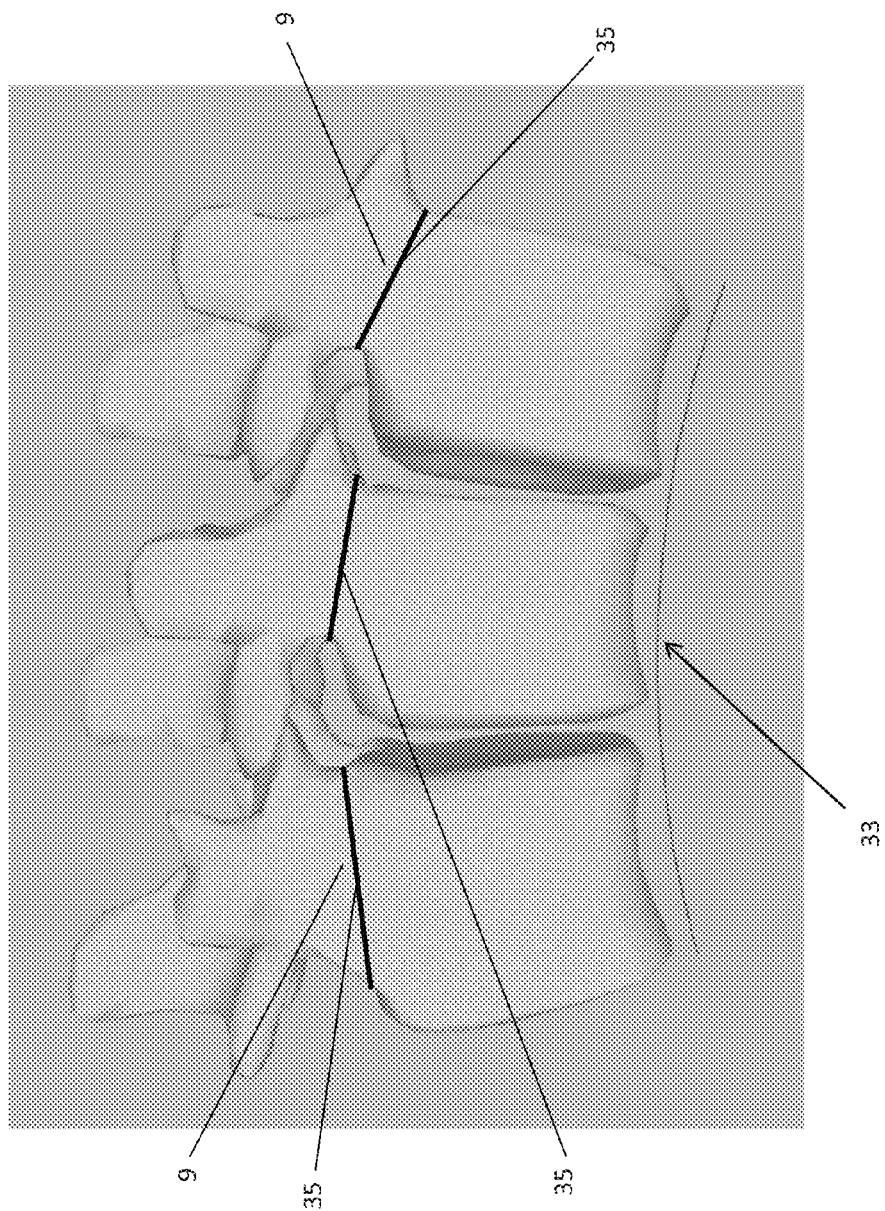

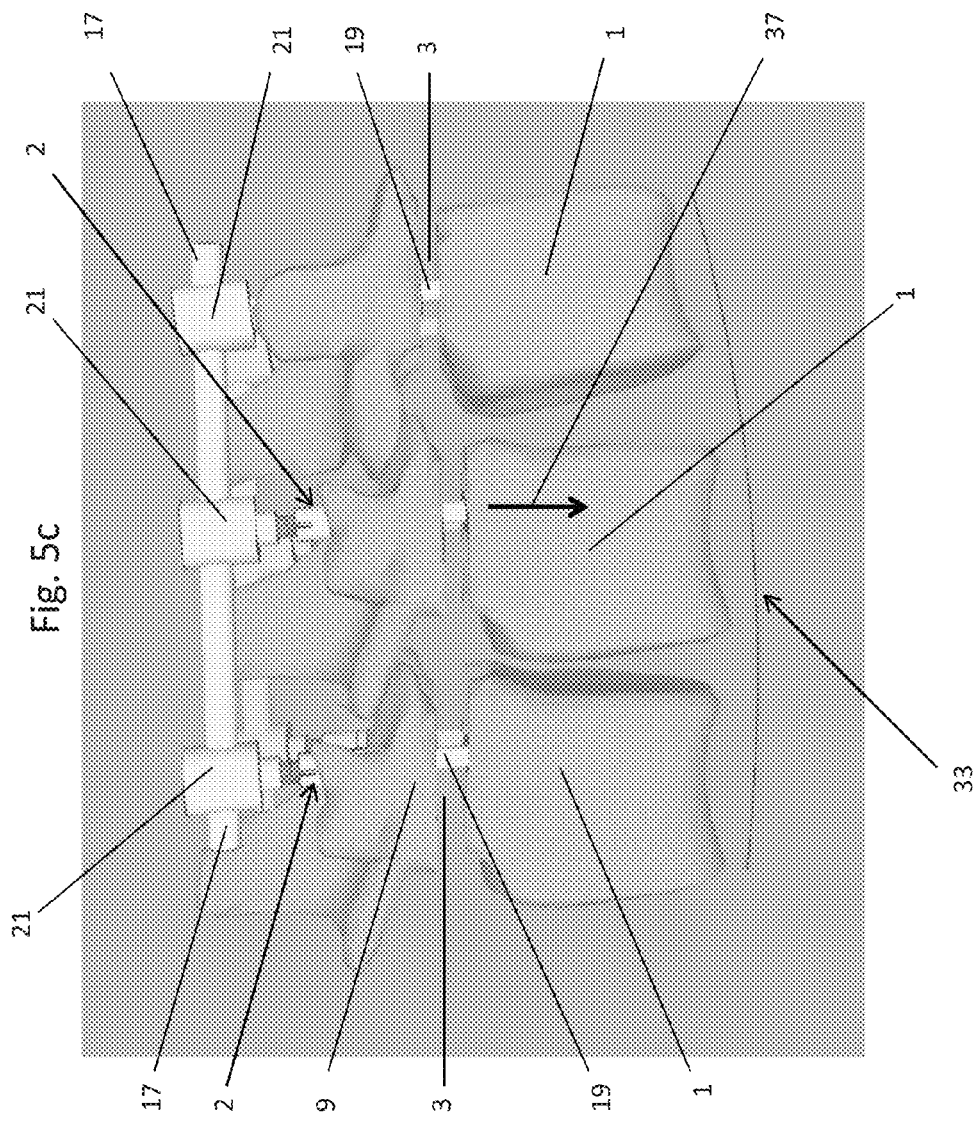

DEVICE AND METHOD FOR EXPANDING THE SPINAL CANAL WITH SPINAL COLUMN STABILIZATION AND SPINAL DEFORMITY CORRECTION

RELATED APPLICATIONS

This application is a continuation-in-part (CIP) of U.S. Ser. No. 12/624,946, filed Nov. 24, 2009; which application is a continuation-in-part (CIP) of U.S. Ser. No. 11/656,790, filed Jan. 22, 2007; which application is a continuation of U.S. Ser. No. 10/102,525, filed Mar. 19, 2002 (now U.S. Pat. No. 7,166,107).

This application also claims benefit of U.S. Provisional Application Ser. No. 61/318,441, filed Mar. 29, 2010. U.S. Ser. No. 12/624,946, filed Nov. 24, 2009, claims benefit of U.S. Provisional Application Ser. No. 61/117,726, filed Nov. 25, 2008. All of the above-identified related applications are incorporated herein by reference.

FIELD OF THE INVENTION

The present invention relates generally to spinal surgery, and more particularly to a method and device for expanding the spinal canal when treating spinal stenosis and for simultaneously providing fixation between vertebrae for fusion and non-fusion applications; namely, for correction of certain spinal deformities, such as kyphosis, scoliosis or a rotation deformity of the spinal column.

BACKGROUND OF THE INVENTION

Spinal stenosis is a common disease involving narrowing of the spinal canal. This disease leads to compression of the spinal nerves and produces symptoms of leg or back pain, walking problems, weakness and/or numbness in the affected portions of the body. Many patients with spinal stenosis also have co-existent spinal problems such as a spinal deformity or spinal instability.

Recently, pedicle lengthening methods and implants have been described for the treatment of spinal stenosis in U.S. Pat. No. 7,166,107, issued Jan. 23, 2007, entitled "Percutaneous Technique and Implant for Expanding the Spinal Canal;" and U.S. application Ser. No. 12/624,946, filed Nov. 24, 2009, (US Publication No. 2010/0168751), entitled "Method, Implant & Instruments for Percutaneous Expansion of the Spinal Canal." In this US patent and US patent application, pedicle lengthening methods and implants (or devices) for expanding a stenotic spinal canal have been disclosed. U.S. Pat. No. 7,166,107, and U.S. application Ser. No. 12/624,946 (US Publication No. 2010/0168751), are incorporated herein by reference.

Although spinal canal expansion through pedicle lengthening allows a novel method for treating spinal stenosis, some patients with severe spinal deformities due to spondylolisthesis, kyphosis, scoliosis or a major rotational deformity of the spinal column may require stabilization of the spinal column, with or without a spinal fusion. For the patient with a combination of spinal stenosis and instability, it would be desirable to decompress (expand) the spinal canal using pedicle lengthening and to achieve simultaneous fixation of the spine to perform the necessary stabilization. To stabilize the spine, the surgeon requires an implant that bridges across one or more vertebral segments using a longitudinal member, such as a plate or rod. By a novel modification of the pedicle lengthening implant, connection to a longitudinal member can be achieved allowing simultaneous expansion of the spinal canal with stabilization of the spinal segment.

Another problem that the current invention addresses is the patient who has undergone pedicle lengthening for the treatment of spinal stenosis in the past and develops instability or a significant spinal deformity that requires stabilization of the lengthened spinal segments. In this situation, it is desirable to use the already present spinal anchors (pedicle lengthening devices) as a point of fixation for the required spinal reconstructive procedure. By providing a novel means of attaching a longitudinal member (rod or plate) to the existing pedicle lengthening devices, this problem can be easily treated without the need to remove the pedicle lengthening devices.

Another problem that the current invention addresses is the need for an improved correction means when treating certain spinal deformities such as kyphosis, scoliosis or a rotational deformity. Current techniques for correcting these deformities are either marginally effective or highly invasive. The current invention provides a novel means to correct these deformities and to simultaneously allow a spinal stabilization procedure to be performed, thus reconstructing the spine in an optimized fashion.

Another problem that the current invention addresses is the need for a biomechanically stronger fixation technique to be used in situations of poor bone quality (osteopenia or osteoporosis) or when major forces need to be applied to the spine. Current techniques for fixation of poor quality bone have major drawbacks and in many cases are marginally effective. The current invention provides a very strong bone anchor that allows secure fixation that can be incorporated into a spinal stabilization construct.

The current disclosure describes a novel medical device and technique for lengthening of the pedicles to correct spinal stenosis while simultaneously allowing connection to a longitudinal member such as a rod or plate for spinal stabilization through either fusion or non-fusion techniques. In addition, this disclosure describes a method and device to convert an existing pedicle lengthening device for attachment of a longitudinal member such as a rod or plate. Also, this disclosure describes the use of the pedicle lengthening device with an attached longitudinal member such as a plate or rod as a means to correct a kyphotic or rotational deformity of the spinal column. Finally, this disclosure describes the use of the pedicle lengthening device as a biomechanically superior bone anchor for use in a spinal fixation construct.

SUMMARY OF THE INVENTION

The present invention comprises a novel medical device capable of lengthening the spinal pedicle and securing the pedicle to a longitudinal member such as a rod or plate to achieve fixation of two or more vertebrae. The current invention is capable of correcting a narrowed spinal canal, while allowing the vertebral segment to be incorporated into a spinal stabilization construct. In addition, the device is useful when treating deformed spines (particularly those spines with excessive kyphosis, scoliosis or a rotational deformity) and provides a biomechanically superior vertebral anchorage compared to the use of a traditional pedicle screw.

Embodiments of the present invention will be shown variously to:

allow expansion of the spinal canal (for the correction of spinal stenosis) and to allow fixation of the involved vertebra into a spinal stabilization construct;

provide an improved ability to correct a spinal deformity (particularly scoliosis, kyphosis or a rotational deformity) while allowing longitudinal fixation of the spinal column;

allow a surgeon to connect a longitudinal member (such as a plate or rod) onto a pedicle lengthening device so that a stabilization procedure can be performed at the site of a prior pedicle lengthening without the need to remove or revise the pedicle lengthening device;

allow a minimally invasive method to achieve both correction and stabilization of the spinal column; and provide a biomechanically superior spinal anchor for use during spinal reconstructive procedures.

In one aspect of the present invention, a novel attachment mechanism is described for the pedicle lengthening device to allow the device to incorporate a longitudinal member (such as a rod or plate) and thus be incorporated into a spinal stabilization construct.

In another aspect, a rod attachment mechanism is described which would allow a previously placed device to be incorporated into a spinal fixation construct.

In yet another aspect, a pedicle lengthening device is shown to correct a rotational or kyphotic deformity of the spinal column.

The present invention has many advantages over currently known methods for treating spinal instability, as would be seen with spondylolisthesis, kyphosis, scoliosis or a rotational deformity, including:

(1) both the correction of spinal stenosis and stabilization of the spinal column can be performed through a single device allowing a much broader range of spinal pathology to be addressed;

(2) an existing pedicle lengthening device can be used as a spinal anchor for a spinal stabilization procedure;

(3) spinal deformities such as kyphosis, scoliosis and rotational deformities can be corrected using the pedicle lengthening technique while allowing the pedicle lengthening device to act as a spinal anchor and be incorporated into a spinal fixation construct;

(4) a biomechanically stronger spinal anchor is provided that can be used to attach a longitudinal member (such as a rod or plate) to the spine; and (5) a minimally invasive spinal device is provided that can produce both decompression of stenotic regions of the spinal canal in addition to spinal fixation for a spinal stabilization procedure; both procedure being achieve through small or percutaneous incisions.

BRIEF DESCRIPTION OF THE DRAWINGS

The drawings included herein are included for the purpose of illustrating preferred embodiments of the current invention; however, it should be clear that the invention is not limited to the precise arrangements or specific parts. Nor is the specific sequence of steps shown required to practice the disclosed invention. All drawings are hereby included for illustration purposes only and in no way should limit the scope of the invention.

FIG. 4a illustrates an axial perspective view of a vertebra with a rotation deformity;

FIG. 4b illustrates an axial perspective view of the vertebra of FIG. 4a following correction of the rotation deformity by pedicle lengthening, in accordance with one embodiment of the invention, and stabilization of the vertebra to an adjacent vertebra;

FIG. 5a illustrates a three segment portion of a spine with a kyphotic deformity;

FIG. 5b illustrates the three segment portion of the spine of FIG. 5a, demarcating locations of corrective pedicle osteotomies; and FIG. 5c illustrates the three segment portion of the spine of FIG. 5a following correction of the kyphotic deformity by pedicle lengthening, in accordance with one embodiment of the invention, and stabilization of the three segment portion by securing the pedicle lengthening implants with a longitudinal member (rod).

DETAILED DESCRIPTION OF THE ILLUSTRATED EMBODIMENTS

Figure 1:
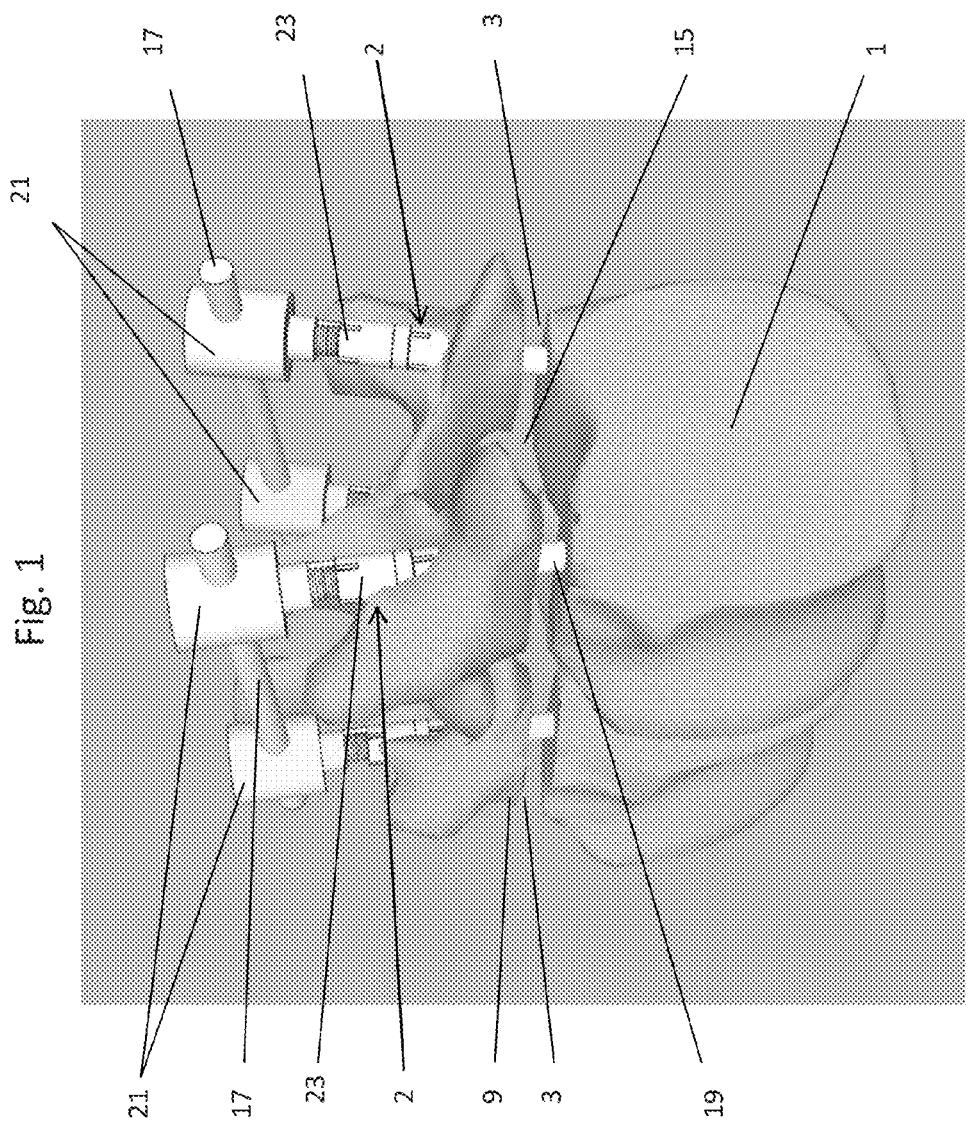
FIG. 1 illustrates a perspective view of a pedicle lengthening and stabilization construct, in accordance with one embodiment of the present invention, implanted within two adjacent vertebrae that have undergone pedicle lengthening.

Referring now to the figures, where like numerals indicate like elements, there is shown in FIG. 1 a perspective view of a pedicle lengthening and stabilization construct, in accordance with one embodiment of the present invention, implanted within two adjacent vertebrae that have undergone pedicle lengthening. Pedicle lengthening implants 2 can be seen implanted into the pedicles 9 of the two adjacent vertebrae.

The pedicle lengthening implants 2 have been extended to create a gap 3 at the base of the pedicle 9 and thus expand the dimensions of the spinal canal 15. Techniques and implants (devices) for pedicle lengthening have been described in detail in U.S. Pat. No. 7,166,107, issued Jan. 23, 2007, entitled "Percutaneous Technique and Implant for Expanding the Spinal Canal;" and in U.S. application Ser. No. 12/624,946, filed Nov. 24, 2009, (US Publication No. 2010/0168751), entitled "Method, Implant & Instruments for Percutaneous Expansion of the Spinal Canal." U.S. Pat. No. 7,166,107, and U.S. application Ser. No. 12/624,946 (US Publication No. 2010/0168751), are incorporated herein by reference.

The pedicle lengthening implants 2 are seen attached to screw head connectors 21, capable of accommodating and securing rods 17 that link the pedicle lengthening implants 2 together, thus securing and stabilizing the attached vertebrae. Also shown in FIG. 1 is locking mechanism 23, that secures each pedicle lengthening implant 2 in its extended position.

Figure 2:
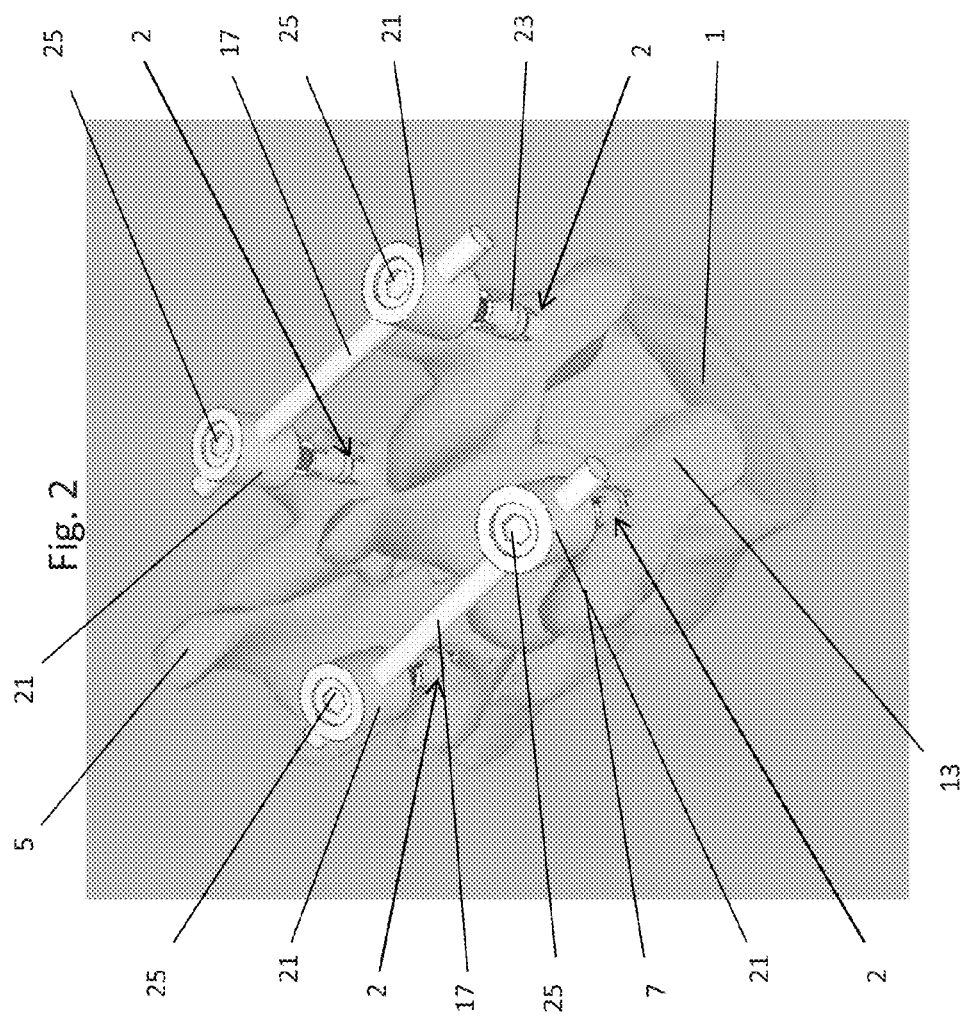
FIG. 2 illustrates a perspective top view of the FIG. 1 embodiment, shown stabilizing two adjacent vertebrae through a rod linkage.

FIG. 2 illustrates a perspective top view of the FIG. 1 embodiment, shown stabilizing two adjacent vertebrae through a rod linkage. In FIG. 2, an upper portion of the pedicle lengthening implants 2 can be seen. Also shown is secure attachment of each screw head connector 21 to a respective rod 17, thereby linking and securing adjacent vertebrae via attachment of the adjacent pedicle lengthening implants 2. The rods 17 are secured into respective screw head connector 21 by a locking nut 25.

Figure 3:
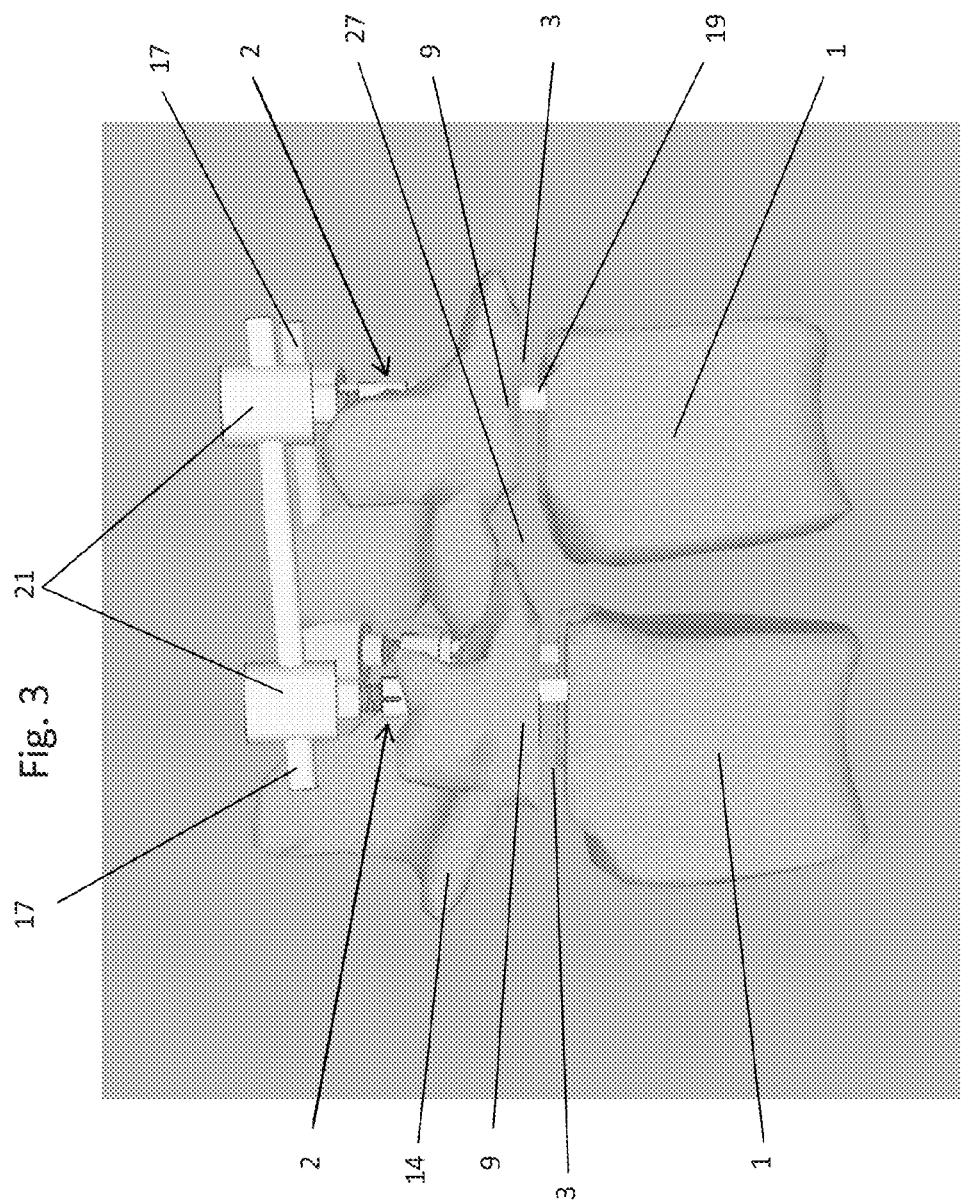
FIG. 3 illustrates a perspective side view of the FIG. 1 embodiment, again showing stabilization of two adjacent vertebrae that have undergone pedicle lengthening.

FIG. 3 illustrates a perspective side view of the FIG. 1 embodiment, again showing stabilization of two adjacent vertebrae that have undergone pedicle lengthening. Pedicle lengthening implants 2 are shown implanted within the pedicles 9 of two adjacent vertebrae. The pedicle lengthening implants 2 have been expanded to lengthen the pedicles 9 and thus expand the spinal canal 15 (shown in FIG. 1) and the neural foramen 27. The pedicle lengthening implants 2 each have attached thereto a screw head connector 21, secured to a rod 17 that spans a joint between the two vertebrae, thus stabilizing the spinal segment.

FIG. 4a illustrates an axial perspective view of a vertebra with a rotation deformity. It will be evident to one skilled in the art of spinal surgery that there is an asymmetry to the vertebra illustrated in FIG. 4a, where a smaller pedicle gap 3 is shown on the right side of the vertebra (as shown in FIG. 4a) and a larger pedicle gap 3 is shown on the left side. The spinous process 5, lamina 11, and the vertebral body 1 of the vertebra also exhibit a rotationally deformed morphology. It should be clear that this type of deformity is common to patients with spinal curvature (scoliosis). In FIG. 4a, pedicle lengthening implants 2, each including jack screws 19 and ventral implants 29, are shown implanted into the pedicles 9 of each vertebra. The jack screw 19 portion of the pedicle lengthening implant 2 is shown extending from the dorsal surface of the pedicle lengthening implants 2.

FIG. 4b illustrates an axial perspective view of the vertebra of FIG. 4a following correction of the rotation deformity by pedicle lengthening, in accordance with one embodiment of the invention, and after stabilization of the vertebra to an adjacent vertebra. In FIG. 4b, it will be evident to one skilled in the art that the rotation deformity shown in FIG. 4a has been corrected and that symmetry has been restored. By differential turning of the jack screws 19, the pedicle gaps 3 have been equalized and a normal relationship between the spinous process 5 and the vertebral body 1 has been created. The rotational deformity correction gained through the use of the pedicle lengthening implants 2 has been stabilized by the attachment of screw head connectors 21 and rods 17, which have been secured to maintain the spine in the corrected state. Also shown is locking mechanism 23, used to secure each pedicle lengthening implant 2 in its extended position.

FIG. 5a illustrates a three segment portion of a spine with a kyphotic deformity. The basic anatomic components of the vertebra, including spinous process 5, transverse process 7, superior articular process 13, inferior articular process 14, pedicle 9 and vertebral body 1 are shown, as well as the neural foramen 27 that allows the nerve root to exit the spinal canal. The posture of the three vertebral segments is seen to curve anteriorly, as shown by arc 33, thus representing a kyphotic deformity.

FIG. 5b illustrates the three segment portion of the spine of FIG. 5a, demarcating the location of corrective pedicle osteotomies. Lines 35 along the base of each pedicle 9 represent the location of the respective pedicle osteotomy, to allow for deformity correction.

FIG. 5c illustrates the three segment portion of the spine of FIG. 5a following correction of the kyphotic deformity by pedicle lengthening, in accordance with one embodiment of the invention, and stabilization of the three segment portion of the spine by securing the pedicle lengthening implants 2 with a longitudinal member (rod 17). Note that the pedicles 9 have been sectioned at their base and the pedicle lengthening implants 2 have been extended to impart an anteriorly directed force vector 37 to the vertebral bodies 1. This anteriorly directed force vector 37 pushes the vertebral body 1 forward to reduce the kyphosis seen in FIGS. 5a and 5b. This sagittal plane curve may be corrected until a lodotic posture arc 33 has been achieved. Stabilization of the deformity correction is shown by the attachment of rods 17 to screw head connectors 21 which have been attached to the pedicle lengthening implants 2.

Method of Operation:

Methods for achieving, and operation of implants to achieve, expansion of the spinal canal, with simultaneous stabilization of the spine, involve, first, cutting and lengthening the pedicles of the pathologically involved vertebral segments. Methods and implants for pedicle lengthening are disclosed in U.S. Pat. No. 7,166,107 and/or U.S. application Ser. No. 12/624,946—each incorporated herein by reference. The pedicle lengthening implants 2 can be implanted, and the necessary expansion of the spinal canal 15 can be achieved through the threadable movement of the jack screw 19 of the pedicle lengthening implant 2, until the desired expansion of the spinal canal is achieved. Next, a locking mechanism 23 is threadably applied to each pedicle lengthening implant 2 to secure the pedicle lengthening implant 2 in its expanded state. A screw head connector 21 is attached to each pedicle lengthening implant 2. Attachment of the screw head connector 21 to the jack screw 19 is achieved using methods well known in the art of spinal surgery. Next, a longitudinal member, such as a rod 17 or plate, is attached to the screw head connector 21 and secured with a locking nut 25 or a similar securing/locking mechanism.

Aspects of the present invention can also be used to attach a longitudinal member (rod 17 or plate) to existing pedicle lengthening implants 2 (i.e., pedicle lengthening implants inserted by a prior surgery). In this situation, the screw head connector 21 is attached to a dorsal portion of the prior pedicle lengthening implant 2. A rod 17 (or similar longitudinal member) can then be attached to the screw head connector 21 and secured with a locking nut 25 or a similar securing/locking mechanism.

When aspects of the present invention are used to correct a rotational deformity, the pedicle lengthening implants 2 should first be inserted into the pedicles 9 (as detailed and referenced above) of the rotationally deformed vertebra. After cutting both the right and left pedicles 9, the pedicles 9 are lengthened in an asymmetric fashion, so that the shorter pedicle 9 is lengthened more than the longer pedicle 9. In some cases, the longer pedicle 9 may actually be maintained without lengthening, while the shorter pedicle 9 is lengthened to achieve the desired degree of rotational correction. Once the desired degree of rotational correction is achieved, the locking mechanism 23 is applied to the jack screw 19, to keep the pedicle lengthening implant 2 in the desired expanded position. In cases where the rotation deformity is part of a major spinal curve such as scoliosis, the pedicle lengthening devices 2 should then be attached to longitudinal members (rods 17 or plates) to stabilize and correct the spinal curvature. To achieve corrected curvature, a screw head connector 21 is attached to a dorsal portion of each pedicle lengthening implant 2. The screw head connectors 21 are then attached to rods 17, or other longitudinal members, and are secured to the rods 17 with a locking nut 25 or to a similar securing/locking mechanism.

When aspects of the present invention are used to correct kyphosis of the spine, pedicle lengthening implants 2 are first implanted into the pedicles 9 of a kyphotic segment of the spine. During the pedicle lengthening maneuver, the pedicles 9 of the vertebrae at the apex of the deformity are lengthened the most, with slightly less lengthening done at the vertebrae adjacent to the apex of the deformity. By lengthening the pedicles 9, an anteriorly directed force vector 37 is produced, which moves the vertebral bodies 1 in an anterior direction, resulting in correction of the kyphotic deformity. Once the desired degree of correction is achieved, the locking mechanism 23 is applied to maintain the pedicle lengthening device 2 in the desired expanded position. Next, screw head connectors 21 are attached to a dorsal portion of the pedicle lengthening implants 2 (as mentioned above). The screw head connectors 21 can then be attached to rods 17, or to other longitudinal members, and are secured with a locking nut 25 or to a similar securing/locking mechanism.

What is claimed is:

1. An implant system for expanding a spinal canal and stabilizing vertebrae, the implant system comprising:
   a pedicle lengthening implant inserted into a first vertebra, the pedicle lengthening implant comprising:
      an outer sleeve having an upper portion and a lower portion; and
      an inner member communicating with the outer sleeve, wherein movement of the inner member in relation to the outer sleeve causes the inner member to translate the upper portion away from the lower portion, about a vertebral cut, to widen the vertebral cut and to thereby expand the spinal canal; and
   a longitudinal member attached to the pedicle lengthening implant, the longitudinal member also communicating with an implant inserted in a second vertebra to fixate the first vertebra to the second vertebra.

2. The implant system of claim 1, further comprising a locking mechanism, applied to the pedicle lengthening implant after operating the pedicle lengthening implant to widen the vertebral cut, the locking mechanism applied dorsal of and abutting the upper portion, to secure the pedicle lengthening implant and the widened vertebral cut.

3. The implant system of claim 1, further comprising a screw head connector attached to a dorsal portion of the pedicle lengthening implant to attach the longitudinal member to the pedicle lengthening implant, wherein the longitudinal member is attached to the screw head connector.

4. The implant system of claim 3, wherein the screw head connector includes a securing mechanism therein to secure the longitudinal member to the screw head connector after inserting the longitudinal member through an opening in the screw head connector.

5. The implant system of claim 4, wherein the securing mechanism is a locking nut within a dorsal end of the screw head connector.

6. The implant system of claim 1, wherein the longitudinal member communicates with the second vertebra by attachment to a respective second pedicle lengthening implant implanted in the second vertebra.

7. The implant system of claim 6, wherein a spinal deformity is manipulated, through operation of the first or the second pedicle lengthening implant, respectively within the first or the second vertebra, to improve a relative relationship between the first and the second vertebra, and the longitudinal member then fixates the first and the second vertebra into a multi-level spinal construct.

8. The implant system of claim 7, wherein attachment of the longitudinal member to the first and the second pedicle lengthening implant treats one or more of kyphosis, scoliosis or rotational deformity of a spine.

9. The implant system of claim 1, wherein the inner member threadably engages at least a portion of an inner channel of the outer sleeve.

10. A method for expanding a spinal canal and stabilizing vertebrae, the method comprising the steps of:
    drilling a passage into a first vertebra;
    performing a cut generally perpendicularly to the passage through the first vertebra;
    inserting the pedicle lengthening implant of claim 1, or claim 9, into the passage;
    operating the pedicle lengthening implant to widen the cut; and
    attaching a longitudinal member to the pedicle lengthening implant, wherein the longitudinal member also communicates with an implant inserted in a second vertebra to fixate the first vertebra to the second vertebra.

11. The method of claim 10, repeated in a second vertebra, wherein operating a second pedicle implant of claim 1, or claim 9, widens a cut in the second vertebra, and attaching the longitudinal member to the respective pedicle lengthening implants fixates the first vertebra to the second vertebra, to correct one or more of a rotational deformity of a vertebra, a kyphotic deformity of a spinal column, and scoliosis of a spinal column.

12. The method of claim 10, wherein a deformity is manipulated, through operation of one or both of the respective pedicle lengthening implants, within the first and/or the second vertebra, to improve a relative relationship between the first and the second vertebra, and the longitudinal member then fixates the first and the second vertebras into a multi-level construct.

13. The implant system of claim 1, wherein the upper portion and the lower portion include external threads to engage a vertebra about each side of the vertebral cut, the upper portion engaging one side of the vertebral cut and the lower portion engaging another side of the vertebral cut.

14. The implant system of claim 13, wherein the inner member threadably engages an inner channel of the upper portion to translate the upper portion away from the lower portion about the vertebral cut to widen the vertebral cut.

15. The implant system of claim 14, wherein the inner member, after threadably engaging the inner channel of the upper portion, bears against the lower portion, to translate the upper portion away from the lower portion about the vertebral cut to widen the vertebral cut.

16. An implant system for expanding a spinal canal and stabilizing vertebrae, the implant system comprising:
    a pedicle lengthening implant inserted into a first vertebra, the pedicle lengthening implant including:
       an upper portion and a lower portion, each having an inner bore;
       an inner member extending into the inner bore of, and interacting with, each of the upper and the lower portions, the inner member extending therein generally defining an implant longitudinal axis; wherein:
       rotating the inner member about the implant longitudinal axis translates the upper portion away from the lower portion, along the implant longitudinal axis, about a vertebral cut, to widen the vertebral cut, thereby expanding the spinal canal; and
    a longitudinal member attached to the pedicle lengthening implant, the longitudinal member also communicating with an implant inserted in a second vertebra to fixate the first vertebra to the second vertebra.

17. The implant system of claim 16, further comprising a locking mechanism, the locking mechanism threadably engaging the pedicle lengthening implant, dorsal of and abutting the upper portion, to secure the upper portion relative to the lower portion along the inner member, about the widened vertebral cut.

18. The implant system of claim 16, further comprising a screw head connector attached to a dorsal portion of the pedicle lengthening implant to attach the longitudinal member to the pedicle lengthening implant, wherein the longitudinal member is attached to the screw head connector.

19. The implant system of claim 16, wherein an externally threaded proximal member extends dorsally from the pedicle lengthening implant, along the implant longitudinal axis.

20. The implant system of claim 19, further comprising a locking mechanism, the locking mechanism threaded internally to engage the proximal member, and threadably translate about the proximal member, along the implant longitudinal axis, to abut the upper portion, to secure the upper portion relative to the lower portion on the inner member.

21. The implant system of claim 20, further comprising a screw head connector threadably receiving the proximal member, the screw head connector receiving therethrough the longitudinal member.

22. The implant system of claim 21, wherein the screw head connector further comprises a locking nut within a dorsal end thereof to secure the longitudinal member therein.

23. The implant system of claim 16, wherein the inner member extends completely through and dorsally from the inner bore of the upper portion, and wherein a locking mechanism, engages the dorsally extending inner member to abut the upper portion, and to secure the upper portion relative to the lower portion on the inner member.

* * * * *